United States Patent [19]

Waterbury et al.

[11] Patent Number: 4,477,460
[45] Date of Patent: Oct. 16, 1984

[54] TOPICAL TREATMENT OF OCULAR HYPERTENSION

[75] Inventors: L. David Waterbury, San Mateo; A. Peter Roszkowski, Saratoga, both of Calif.

[73] Assignee: Syntex (U.S.A.) Inc., Palo Alto, Calif.

[21] Appl. No.: 435,195

[22] Filed: Oct. 19, 1982

[51] Int. Cl.³ .......................................... A61K 31/425
[52] U.S. Cl. ..................................................... 424/270
[58] Field of Search ......................................... 424/270

[56] References Cited

U.S. PATENT DOCUMENTS

| | | | |
|---|---|---|---|
| 3,709,992 | 1/1973 | Schmeling et al. | 424/270 |
| 3,850,945 | 11/1974 | Edwards | 260/302 R |
| 3,897,441 | 7/1975 | Edwards | 424/270 |
| 3,982,010 | 9/1976 | Edwards | 424/270 |
| 4,064,258 | 12/1977 | Lewis et al. | 424/266 |
| 4,259,341 | 3/1981 | Baldwin et al. | 424/270 |

OTHER PUBLICATIONS

Glaucoma Update-Krieglstein (ed.)-pp. 19-26 (1979).

*Primary Examiner*—Douglas W. Robinson
*Attorney, Agent, or Firm*—Hana Dolezalova; Tom M. Moran; Alan M. Krubiner

[57] ABSTRACT

This invention concerns the novel use of certain known thiazoles, particularly acylaminothiazoles and thiazolecarboxamides, as intraocular pressure lowering agents. When administered topically to the eye with increased intraocular pressure the compounds are effective in decreasing intraocular pressure, in preventing development of acute or chronic ocular hypertension including glaucoma, in inhibiting the further deterioration of the eye due to intraocular hypertension, or in relieving the symptoms of already existing ophthalmic disease.

11 Claims, No Drawings

TOPICAL TREATMENT OF OCULAR HYPERTENSION

BACKGROUND OF THE INVENTION

1. Field of the Invention

This invention relates to a novel method for a treatment of ophthalmic diseases associated with increased intraocular pressure. Certain known compounds have been found to lower intraocular pressure in mammals and would, therefore, be useful in the treatment of glaucoma or other ophthalmic diseases which are accompanied with or caused by increased intraocular pressure.

2. Related Disclosures

Intraocular pressure is as constant for the organism as is temperature, pulse, and blood pressure. Like many other autonomic body functions, it has a circadian rhythm over 24 hours with a sinusoidal up and down pattern. A constant intraocular pressure within the limits of circadian fluctuation (15-20 mm Hg) is a prerequisite for normal visual function and it is tied to the normal relationship between cornea, lens, and retina as well as to the clarity of media. In the interest of vision, under the normal circumstances, every elevation of intraocular pressure is immediately offset in the opposite direction by regulatory mechanisms. Certain local and central nervous functions insure that the equilibrium is immediately re-established. *Ophthalmology*, Fritz Hollwich, George Thieme Publishers, 127, (1979).

Many ophthalmic diseases are ocular disorders which are either caused by or associated with increased intraocular pressure. Such complications very often lead to an impairment of the eyesight or blindness. Among those diseases considered most dangerous which are associated with increased intraocular pressure belongs a group of ocular diseases called glaucoma.

Glaucoma is a group of ocular diseases with common features of abnormally elevated intraocular pressure which slowly causes progressive loss of peripheral visual fields. When untreated, glaucoma causes a loss of central vision and ultimate blindness. A number of diverse clinical cases are included in the category of glaucoma. The causes of the development of glaucoma are mostly unknown. Glaucoma is usually treated topically by agents which constrict the pupil of the eye, such as pilocarpine or carbachol, systemically by osmotic agents or carbonic anhydrase inhibitors, or by surgery. *The Merck Manual*, 13th Ed., 1702, (1977).

To define glaucoma in its simplest form, one can state that there is an intraocular pressure elevation which rests upon an imbalance between aqueous inflow and outflow. The etiology of this imbalance is highly variable.

The glaucoma is generally categorized as primary, secondary, congenital and absolute, and these categories are described in detail in *The Merck Manual* cited above.

Primary glaucoma is generally sub-classified into two categories, chronic simple (open-angle) glaucoma and acute or chronic congestive (angle-closure) glaucoma.

Chronic simple open-angle glaucoma is the most prevalent form of glaucoma, and the one which will be most responsive to a treatment of topical administration of the compounds of this invention. It is a disorder characterized by a gradual rise in intraocular pressure, causing slowly progressive loss of peripheral vision and, when uncontrolled, late loss of central vision and ultimate blindness. The reason for increased ocular pressure in open angle glaucoma is that outflow of aqueous trabecular meshwork into Schlemm's canal is retarded and the resistance to aqueous outflow is elevated. Hence, the intraocular pressure is also elevated.

A congestive angle-closure glaucoma is subdivided into acute angle-closure and chronic angle-closure glaucoma.

Acute angle-closure glaucoma is a disorder characterized by attacks of suddenly increased intraocular pressure to three to five times normal values which occurs over a period of a few hours. The reason for increased intraocular pressure is an acute blockage of aqueous outflow. Each acute attack progressively diminishes vision and contracts the visual field.

Chronic angle-closure glaucoma is a disorder characterized by recurrent attacks, usually unilateral, of increased intraocular pressure, pain, and impaired vision—similar to those of acute angle-closure glaucoma, but less severe.

Secondary glaucoma is usually a product of numerous underlying diseases such as intraocular inflammation, perforating injuries with lesions to the ciliary body, a development of anterior synechiae, swelling or luxation of the lens, vascular diseases and others.

Absolute glaucoma is the last stage of any form of uncontrolled glaucoma. The eye is blind from progressive atrophy of the optic nerve head.

Presently predominant medical treatment of all types of primary glaucoma (simple open-angle, acute angle-closure and chronic glaucoma) is a topical administration of pilocarpine timolol maleate, or cholinesterase inhibitors including eserine. The goal of this therapy is to lower the intraocular pressure. Other systemic medications such as acetazolamide, an enzyme inhibitor which acts specifically on carbonic anhydrases, are available for treatment of glaucoma. In the eye, inhibitory action of acetazolamide decreases the secretion of aqueous humor and results in a drop in intraocular pressure, a reaction considered desirable in cases of glaucoma. Other forms of glaucoma may be treated similarly, i.e. by topical administration of pilocarpine, eserine, timolol maleate, corticosteroids or anti-inflammatory agents, or systemically by carbonic anhydrase inhibitors. All forms of glaucoma may be treated surgically. *PDR*, 36th Ed., 1046, (1982).

The goal of topical and systemic therapy of glaucoma is to decrease the intraocular pressure. Existing therapy, especially topical therapy with pilocarpine, eserine or timolol, however, require the strong, high percentage topical drops applied in rather short time periods. Moreover, many of the topically used drugs also have undesirable systemic secondary effects.

Attempts to find effective treatment of ocular hypertension are known. Catecholamine treatment of ocular hypertension is described in U.S. Pat. No. 4,275,074. Treating glaucoma and lowering intraocular pressure by topical administration of R,R-labetalol is described in U.S. Pat. No. 4,312,863. N-Demethylated carbachol reducing intraocular pressure in glaucomatous dogs is described in *Invest. Ophthalmic Vis. Sci.*, 19:1198 (1980). U.S. Pat. No. 4,322,425 describes an ophthalmic composition containing a carbostyril derivative useful for treatment of glaucoma.

Applicants have found that certain known thiazoles, particularly acylaminothiazoles and thiazolecarboxamides, are useful for decreasing intraocular pressure when applied topically to the eye and hence, useful for treatment, prevention or inhibition of primary or secondary glaucoma or any other ophthalmic disease which is associated with or caused by ocular hypertension. These compounds show high potency to decrease intraocular pressure comparable to timolol maleate, which is a commonly used topical intraocular hypotensive. Beside the fact that these compounds are extremely potent when administered topically, they do not cause secondary symptoms usually accompanying the systemic treatment of hypertension in the eye and thus their use is advantageous against other known ocular hypotensive drugs. For example, timolol maleate when applied topically may be absorbed systemically and can cause bronchospastic disease, sinus bradycardia, cardiogenic shock, cardiac failure, etc. *PDR*, 36th Ed., pp. 1284 (1982). On the contrary, compounds of this invention show no systemic activity whatsoever and when applied topically they seem not to be absorbed systemically.

Compounds which are the subject of this invention and those having similar structures to these compounds are known and have been described in U.S. Pat. No. 3,897,441; U.S. Pat. No. 4,064,258; and U.S. Pat. No. 3,850,945. The compounds described in these patents exhibit cardiovascular activities and are useful in the treatment of abnormal heart conditions as well as systemic hypertension in mammals. These compounds were not previously administered topically, i.e., directly to the eye, to prevent, inhibit or treat ophthalmic diseases probably because their non-irritating properties to the eye were unknown, and are unexpected and surprising.

SUMMARY OF THE INVENTION

This invention is a method for the treatment of ophthalmic diseases in mammals, particularly those diseases associated or caused by increased intraocular pressure, which method comprises administering directly to the eye of a mammal in a need thereof a pharmaceutically effective amount of compound chosen from those represented by the formula:

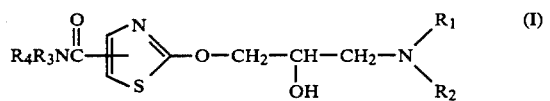

and their pharmaceutically acceptable, non-toxic salts wherein $R_1$ and $R_2$ are each independently selected from the group of hydrogen, lower alkyl, lower cycloalkyl, lower alkenyl, phenyl optionally substituted, and lower phenylalkyl;

$R_3$ and $R_4$ are each independently selected from the group of hydrogen, linear or branched alkyl, cycloalkyl, and phenyl; and wherein $R_4R_3NC(O)$ is a substituent on the thiazole ring at either the 4- or 5-position; or compound chosen from those represented by the formula:

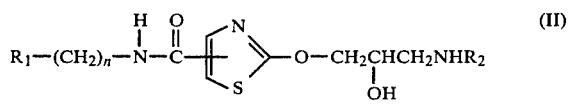

and pharmaceutically acceptable salts thereof wherein n is the integer 2, 3, or 4;

$R_1$ is a carbocycle selected from the group consisting of bicyclo[3.1.0]hexyl, bicyclo[2.2.1]heptyl, adamantyl, and 4-methylbicyclo-[2.2.2]oct-1-yl and wherein attachment to the $(CH_2)_n$ linking group can be at any ring atom of bicyclohexyl, bicycloheptyl, or adamantyl groups and is at the 1-position of the bicyclooctyl group; and $R_2$ is lower alkyl.

The compounds which are particularly valuable in this regard are 1-t-butylamino-3-[5-(5-methylhexylcarbamoyl)-2-thiozolyloxy]-propan-2-ol and (dl)-1-isopropylamino-3-(5-[2-(endo-bicyclo]3.1.0]hex-6-yl)ethylcarbamoyl]-2-thiazolyloxy)-propan-2-ol.

The invention also relates to a pharmaceutical composition and preparation of the pharmaceutical ophthalmic solution for the treatment and prevention of ophthalmic diseases.

DETAILED DESCRIPTION OF THE INVENTION

Definitions

"Alkyl" means a branched or unbranched saturated hydrocarbon chain containing 1–12 carbon atoms, such as methyl, ethyl, propyl, tert-butyl, n-hexyl, octyl and the like.

"Lower alkyl" means a branched or unbranched saturated hydrocarbon chain of 1–6 carbons, such as, for example, methyl, ethyl, n-propyl, i-butyl and the like.

"Optionally substituted lower phenylalkyl" means a moiety in which the phenyl, which may or may not be substituted as described above, is attached to the compounds of this invention by an intervening lower alkyl. Such embodiments of "optionally substituted phenyl lower alkyl", are, for example benzyl, phenylethyl, 2-(4-fluorophenyl)ethyl 3-(3,5-dimethylphenyl)-n-propyl and the like.

"Substituted phenyl" means a phenyl group which has one or two substituents selected from the group of hydroxy, lower alkyl, lower alcoxy or halo groups. Typical substituted phenyl groups include, for example, p-hydroxyphenyl, p-ethylphenyl, p-t-butoxyphenyl and the like.

"Alkenyl" means monoethylenically unsaturated linear or branched acyclic hydrocarbon chain such as propenyl, butenyl, pentenyl, hexenyl and the like.

"Lower alkenyl" means an unsaturated linear or branched alkenyl as defined above with a chain of 1–6 carbons, such as, for example, vinyl (ethenyl), propenyl, butenyl and such.

"Cycloalkyl" means a saturated monocyclic hydrocarbon of 3–7 carbons without side chains, such as cyclopropane, cyclobutane, cyclopentane, cyclohexane and cycloheptane.

"Carbocycle" means a homocyclic ring compound in which all the ring atoms are carbon. Typical carbocycles are benzene, bicyclohexyl, tricyclodecyl and such.

Pharmaceutically acceptable salts refers to pharmaceutically acceptable hydrogen-anion addition salts which do not adversely affect the pharmaceutical properties of the parent compounds. With respect to the addition salts, suitable inorganic anions include, for example, chloride, bromide, iodide, sulfate, phosphate, nitrate, sulfate and the like. Suitable organic anions include, for example, acetate, benzoate, lactate, picrate, propionate, butyrate, valerate, tartrate, maleate, fumarate, citrate, succinate, tasylate, ascorbate, nicotinate, adipate, gluconate and the like.

"Ophthalmic diseases" as used hereinafter mean ocular disorders which are either caused by or associated with increased intraocular pressure and include but are not limited to, all forms of glaucoma as defined in *The Merck Manual* cited above.

"Mammals" means a class of warm-blooded vertebrates characterized by mammary glands, including but not limited to humans, laboratory or domestic animals such as dogs, cats, mice, rats or rabbits, and livestock.

"Treatment" covers any treatment of the disease in a mammal, particularly human, and includes (i) preventing the disease from occuring in a subject which may be predisposed to the disease but has not yet been diagnosed as having it, (ii) inhibiting the disease, i.e. arresting the development of said disease, or (iii) relieving the disease, i.e. causing regression of the disease.

Preferred Embodiments of the Invention

The broadest aspect of this invention is given in the summary of this invention in the specification.

Most preferred and exemplary compounds useful in the method of the present invention include, but are not limited to:
1-t-butylamino-3-[5-(5-methylhexylcarbamoyl)-2'-thiazolyloxy]-propan-2-ol;
1-isopropylamino-3-(5-[2-(endo-bicyclo]3.1.0]-hex-6-yl)ethylcarbamoyl]-2-thiazolyloxy)-propan-2-ol; and their pharmaceutically acceptable non-toxic esters and salts.

Preparation Procedures

Thiazole compounds of formula (I) represented by the compound 1-t-butylamino-3-[5-(5-methylhexylcarbamoyl)-2-thiazolyloxy]-propan-2-ol are disclosed and their detailed preparation is described in U.S. Pat. No. 3,897,441 which is hereby incorporated by reference.

3-Thiazol-2-oxy-aminopropanols of formula (II) represented by the compound 1-isopropylamino-3(5-[2-(endobicyclo[3.1.0]hex-6-yl)ethylaminocarbonyl]-2-thiazolyloxy)propan-2-ol are disclosed and their preparation is described in U.S. Pat. No. 4,064,258 and is hereby incorporated by reference.

Utility and Administration

This invention is directed to a novel method useful for relieving, inhibiting or preventing ophthalmic diseases caused by or associated with increased intraocular pressure. The method is particularly useful in the number of clinical cases included in the category of glaucoma. The method and composition are intended to cover any treatment of the disease in a mammal, particularly human, and includes (i) preventing the disease from occurring in a subject which may be predisposed to the disease but has not yet been diagnosed as having it, (ii) inhibiting the disease, i.e. arresting the development, or (iii) relieving the disease, i.e. causing regression of the disease.

The compounds of this invention and their pharmaceutically acceptable non-toxic alkyl esters and salts have been found, in animal experiments, to be non-irritating, hence physiologically compatible, and yet to have a profound antihypertensive effect on intraocular pressure when applied topically directly to the eye. Thus, these compounds are highly potent in penetrating ocular tissue but, surprisingly, upon their topical application, they are not absorbed into systemic circulation and they show no irritation of the ocular tissue. Accordingly, these compounds, when applied topically, offer a method for treating ocular disorders caused or associated with intraocular hypertension of the mammal without exposing the mammal to undesirable secondary symptoms caused by large dosages required for systemic treatment.

The method of this invention is both curative and preventative. Where applied, for example, to the eye which is showing an acute intraocular pressure deviation but is not as yet diagnosed as glaucoma, it will decrease the elevated intraocular pressure to its normal level and will stabilize it, thus preventing the development of glaucoma. A topical application of appropriate ophthalmic solution with active ingredient to the eye already suffering from glaucoma will stop a further increase in intraocular pressure and further deterioration of vision and it will decrease previously elevated pressure to its normal level without submitting the patient to severe secondary symptoms which may follow, for example, those which may occur upon topical administration of timolol maleate.

The optical function of the eye requires the stability of its dimensions which is provided partly by the fibrous outer coat. A more effective stabilizing factor, however, is the intraocular pressure which is in excess of the pressure prevailing in the surrounding tissues. This intraocular pressure is the result of a steady production of specific fluid, the aqueous humor, which originates from the ciliary processes and leaves the eye by an intricate system of outflow channels. The resistance encountered during this passage and the rate of aqueous production are the principal factors determining the level of the intraocular pressure. In addition to this hydromechanical function, the aqueous humor acts as a carrier of nutrients, substrates, and metabolites for the avascular tissues of the eye.

The human eye is an excellent subject for the topical administration of drugs. The basis of this can be found in the anatomical arrangement of the surface tissues and in the permeability of the cornea. The protective operation of the eyelids and lacrimal system is such that, unless the material is chemically and physiologically compatible with surface tissues, there is rapid removal of material instilled into the eye.

The therapeutic effect of many topically administered (instilled) drugs is contingent upon their absorption from the cul-de-sac into the eye. Drugs which are administered by instillation and which must penetrate into the eye enter primarily through the cornea. This is a much more effective route of administering the drug into the eye than through the conjunctiva and underlying sclera.

The conjunctiva contains many blood vessels and lymphatic vessels. The blood vessels usually dilate when irritation is set up by a foreign body, a microbial infection, or by chemical means. Of the drug molecules which penetrate into the conjunctiva a large proportion enters the blood stream where they may cause undesirable systemic reactions. It is, therefore, important that the administered drug have no systemic activity. Below the conjunctiva lies the sclera, which water-soluble drugs penetrate with ease and which lipoid-soluble drugs penetrate with difficulty.

In the non-inflamed eye, as for example in glaucoma, the blood-aqueous barrier, constituted of the blood vessel wall and various thicknesses of the ocular tissues, prevents certain systemically administered drugs in therapeutic concentrations from reaching the anterior segment.

In the practice, the compounds of the invention or their pharmaceutically acceptable non-toxic esters and salts are administered topically, i.e., directly to the eye of a subject suffering from glaucoma or ocular hypertension. Administration of the drug is in the form of ophthalmic preparation applied directly to the eye.

Ophthalmic preparations are sterile products for either topical application to the eyelids or instillation into the space (cul-de-sac) between the eyeball and the eyelids. Presently available ophthalmic preparations include solutions, suspensions, and ointments. Presently available topical treatment of eye diseases include topically applied ophthalmic drops, solutions, suspensions or ointment or their subconjunctival injection.

Most ophthalmic solutions are so formulated as to mix readily with the lacrimal fluids and spread over the surfaces of the cornea and conjunctiva. With the usual technique of instillation the major portion of the drug is deposited in the lower fornix. Capillarity, diffusional forces, and the blinking reflex are the forces that bring about the incorporation of the drug in the precorneal film from which it penetrates into and through the cornea. Studies have indicated that a substance will pass through the cornea most easily if it has a biphasic solubility; that is, if it is soluble both in fat and in water.

The cornea can be penetrated by ions to a small, but measurable, degree. Under comparable conditions, the permeabilities are similar for all ions of small molecular weight, which suggests that the passage is through the extracellular spaces. The diameter of the largest particles which can pass across the cellular layers seems to be in the range 10–25 A. Increase in the permeability of the cellular layers can be produced by experimental techniques which involve slight manipulations such as touching the cornea, or instilling solutions differing in tonicity from that of the body fluids, or even stirring the solution in contact with the corneal surface. *Remington's Pharmaceutical Sciences*, 15th Ed., 1489–1504 (1975).

The composition of this invention comprises, as active ingredient, a compound of this invention or an ester or salt thereof in admixture with an ophthalmologically acceptable excipient. An excipient is ophthalmologically acceptable if it is non-irritating to the eye and if its active ingredient penetrates the blood-aqueous barrier and/or difuse to or through the various ocular substructures to the site where it is pharmacologically active. The composition may be aqueous or non-aqueous, and it may be in the form of a solution, suspension, gel, ointment, slow release polymer, or other. Amount of active ingredient will vary with the particular formulation and disease state but generally will be between 0.001–10% of active ingredient per individual application dose.

Pharmaceutical ophthalmic compositions are typically sterilized aqueous solutions (i.e. eyedrops) containing 0.001% to 10% wt/vol.; most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives/sterilants are phenylmercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by solutes in a suitable quantity of water, adjusting the pH to about 6.8–8.0, making a final volume adjustment with additional water, and sterilizing the preparation using method known to those in the art.

The dosage level of the resulting composition will, of course, depend on the concentration of the drops, the condition of the subject and the individual magnitude of responses to treatment. However, typical dosage ranges might be about 2–10 drops of 0.1% solution of active ingredient per day.

Most ophthalmic solutions and suspensions contain an aqueous rather than an oily vehicle. Ophthalmic ointments usually contain a white petrolatum-mineral oil base, often including anhydrous lanolin, while some have a polyethylene-gelled mineral oil base.

Solutions are the most commonly used type of preparation for the local medication of eyes. They are easily instilled and rarely cause adverse reactions. The vehicle does not cause interference with vision and does not interfere with regeneration of the corneal epithelium.

Oily solutions such as for medicaments which are incompatible with water are infrequently used. The only official ophthalmic solution using oil is that of isoflurophate.

Suspensions have the advantage of more extended action and the disadvantage that it is difficult to avoid the presence of a few particles which are large enough to cause irritation.

Eye ointments are sterile preparations for application to the conjunctival sac or lid margin. They have advantages of more prolonged contact and effect, hardly any irritation on initial installation, slower movement into lacrimal ducts, greater storage stability, and less likelihood of contamination problems. Their disadvantages are that they produce a film over the eye and thereby blur vision; and they may interfere with the firm attachment of new corneal epithelial cells to their normal base. Ointments affect the outside and edges of the eyelids, the conjunctiva, the cornea, and the iris, depending on their ability to penetrate the outer covering of the eyeball.

Ophthalmic ointments comprising active ingredients can be used for the effect of a variety of medicaments on the outside and edges of the eyelids, the conjunctiva, the cornea, and the iris. Most ophthalmic ointments are prepared with a base of white or yellow petrolatum and mineral oil, often with added anhydrous lanolin. Whichever base is selected, it must be nonirritating to the eye, permit diffusion of the drug throughout the secretions bathing the eye, and retain the activity of the medicament for a reasonable period of time under proper storage conditions.

A suitable basis for eye ointments is given by the following formula:
Liquid Paraffin: 100 g
Wool Fat: 100 g
Yellow Soft Paraffin: 800 g The wool fat, the yellow soft paraffin and the liquid paraffin are heated together, filtered while hot through a course filter paper in a heated funnel, sterilized by heating for a sufficient time to ensure that the whole of the basis is maintained at a temperature of 150° C. for one hour, and allowed to cool, taking precautions to avoid contamination with micro-organisms, before incorporating the sterile medicament.

Eye ointments are prepared, by means of an aseptic technique, by either of the following methods:

Method A.

If the medicament is readily soluble in water forming a stable solution, it is dissolved in the minimum quantity of water and the solution sterilized by Autoclaving or by filtration and incorporated gradually in the melted sterile basis, the mixture being stirred continuously until it is cold. The eye ointment is then transferred to the final sterile containers, which are closed so as to exclude microorganisms.

Method B.

If the medicament is not readily soluble in water or if the aqueous solution is unstable, the medicament is finely powdered, thoroughly mixed with a small quantity of the melted sterile basis, and then incorporated with the remainder of the sterile basis. The eye ointment is then transferred to the final sterile containers, which are closed so as to exclude microorganisms.

If the medicament is insoluble in both water and the basis, it is essential that it be reduced to an extremely fine powder before incorporating with the basis, in order to avoid irritation to the eye.

It is obligatory that ophthalmic ointments do not contain particulate matter that may be harmful to eye tissues. Hence, in preparing such ointments special precaution is taken to exclude or to minimize contamination with foreign particulate matter, e.g., metal particles fragmented from equipment used in preparing ointments, and also to reduce the particle size of the active ingredient(s) to impalpability. The official compendia provide tests designed to limit to a level considered to be unobjectionable the number and size of discrete particles that may occur in ophthalmic ointments.

Testing for sterility of products such as ophthalmic ointments has been greatly facilitated by use of sterile bacteria-retaining membranes (those having a nominal porosity of $0.45\mu$ are commonly used). For ointments soluble in isopropyl myristate (the solvent used in the official test for sterility) a sample of the ointment is dissolved in the sterile solvent and filtered through the sterile membrane which, after washing with sterile rinse medium, is subjected to the sterility test. For ointments insoluble in isopropyl myristate the sample is suspended in a suitable aqueous vehicle that may contain a dispersing agent.

The official compendia direct that ophthalmic ointments be prepared from previously sterilized ingredients, under rigidly aseptic conditions. Petrolatum vehicles and many medicaments may be sterilized by heating in a hot-air oven at 150° C. for 2 hours; utensils required for compounding may be sterilized by autoclaving; empty tubes may be sterilized by storage for 24 hours in a 1:1000 solution of benzalkonium chloride in 70% isopropyl alcohol followed by removal of alcohol by evaporation. A sterile disposable syringe without a needle may be used to transfer the finished ointment, if it is semi-fluid, to the ointment tube, or sterile aluminum foil or powder paper may be used for the same purpose. Probability of microbial contamination is greatly reduced by carrying out selected steps of the procedure in a laminar-flow hood.

Compounds of this invention may also be administered by other nonsystemic modes. Ophthalmic packs may be used to give prolonged contact of the solution with the eye. A cotton pledget is saturated with an ophthalmologically suitable solution and this pledget is inserted into the superior or inferior fornix. Packs are commonly used to produce maximal mydriasis. In this case the cotton pledgets can be, for example, saturated with a solution of a compound of this invention. Medicated ophthalmic disks produce mitosis both more intense and prolonged than either solution. Use of disks may be preferable to use of solutions.

The compounds may also be administered by the way of iontophoresis. This procedure keeps the solution in contact with the cornea in an eyecup bearing an electrode. Diffusion of the drug is effected by difference of electrical potential.

Subconjunctival injections of compounds of the current invention may be used to introduce medications which, if instilled, either do not penetrate into the anterior segment or penetrate too slowly for the desired effect. The conjunctival membrane covers the outer surface of the white portion of the eye and the inner aspect of the eyelids. In most places it is loosely attached and thereby permits free movement of the eyeball. This makes possible subconjunctival injections. The drug is injected underneath the conjunctiva and propably passes through the sclera and into the eye by simple diffusion. The most common use of subconjunctival injection is for the administration of antibiotics in infections of the anterior segment of the eye. Subconjunctival injections of mydriatics and cycloplegics are also used to achieve maximal pupillary dilation or relaxation of the ciliary muscle. If the drug is injected underneath the conjunctiva and the underlying Tenon's capsule in the more posterior portion of the eye, effects on the ciliary body, choroid, and retina can be obtained.

Drugs may also be administered by retrobulbar injection whereby they enter the globe in essentially the same manner as the medications given subconjunctivally. The orbit is not well vascularized and the possibility of significant via blood stream effects of retrobulbar injections is very remote. In general, retrobulbar injections are given for the purpose of getting medications into the posterior segment of the globe and to affect the nerves and other structures in the retrobulbar space. *Remington's Pharmaceutical Sciences*, 15th Ed., 1489–1504, (1975).

The following examples are intended to illustrate, but not to limit, the scope of the invention.

EXAMPLE 1

Eye Irritation Study

This example illustrates non-irritating properties of compounds of this invention when used as topical ocular hypotensives administered directly to the eye of an experimental animal.

To be an effective topical ocular hypotensive agent, the compound must, first of all, itself prove to be non-irritating. To determine the effects of various compounds on eye irritation, the comparative irritability test among known ocular hypotensives was designed wherein the irritation of the eye following the topical application of tested compound was measured and compared to the irritation of the eye following the application of other ocular hypotensive compound. Each studied compound was tested individually on a single animal by administering, at the same time, into one eye of the animal the ophthalmic solution with the test compound as an active ingredient and to the other eye only vehicle ophthalmic solution. An irritation, if any, caused by tested compounds was compared to the non-irritating effect of the vehicle ophthalmic solution applied to the other eye. Irritation was measured by the number of blinks of each eye during the same time period. Tests were performed on rats, dogs and monkeys.

Ophthalmic solutions of 1-t-butylamino-3-[5-(methylhexyl carbamoyl)-2-thiazolyloxy]-propan-2-ol as the active ingredient were prepared at the concentrations of 0.02%, 0.1% and 0.5%. One drop of the test ophthalmic solution with active ingredient was administered directly into the conjuctival sack of the rat's left eye. At the same time one drop of vehicle was administered to the conjunctival sack of the rat's right eye. Irritation of each eye was measured by counting the number of blinks for one minute after the application. The results were expressed as the mean number of blinks±standard error per eye. The mean number of blinks/minute were averaged for the vehicle treatment and compared to the drug treated eye. Each compound was tested similarly in mongrel dogs and rhesus monkeys.

The compounds of this invention did not elicit any irritation of the eyes in any of the three species at any concentration which was used for testing (i.e., 0.02–0.5%) and their effects were comparable to the effect of the vehicle ophthalmic solution without any drug added.

EXAMPLE 2

Effect on Increased Intraocular Pressure

This example illustrates the effect of compounds of the current invention on intraocular pressure (IOP).

Intraocular pressure may be artificially elevated by intravenous infusion of glucose according to the method of Bonomi et al, *Glaucoma,* Royal Society of Medicine International Congress and Symposium Series No. 21, p. 99 (1979).

Two groups of Dutch belted rabbits were used for this study. In each group the number of animals was at least 5. One hour prior to infusion of glucose, intraocular pressure of both eyes was measured and then 50 μl of a 1% solution of 1-t-butylamino-3-[5-(methylhexylcarbamoyl)-2-thiazolyloxy]-propan-2-ol as an active substance in saline was instilled in the right eye of each rabbit. Prior to infusion of glucose, intraocular pressure was again measured to ensure that no increase in intraocular pressure occurred after topical administration of the active compound. Then the rabbits were given an infusion of 10 ml of 5% glucose solution/kg of body weight in the marginal ear vein. In all animals the infusion was completed within 60 seconds. Immediately after the end of infusion the eye pressure in both eyes increased, reaching its maximum level between 5 and 10 minutes and returning to the original level within 40 minutes. At the time of the peak effect, i.e. 10 minutes after the glucose infusion, intraocular pressure was again determined.

As expected, glucose infusion increased intraocular pressure in the left eye. The pretreatment of the right eye with the tested drug prevented this hypertension. The difference between the left eye (non-treated) and the right eye (pretreated) intraocular pressures was significant (p<0.05).

EXAMPLE 3

Caffeine Stimulated Increase in Intraocular Pressure

This example illustrates the ability of compounds of the current invention to block an experimentally induced increase in intraocular pressure due to intravenous injection of caffeine. The procedure for this example is the modified procedure of Genee, *Klin. Mbl. Augenheilk,* 160:605,Verlag Stuttgart Publ. (1972).

Female Dutch belted rabbits were divided in two groups with at least 5 rabbits in each group.

Intraocular pressure in both eyes of all rabbits was measured and recorded as mm Hg. 50μl of 0.5% solution of 1-t-butylamino-3-[5-(methylhexyl carbamoyl)-2-thiazolyloxy]-propan-2-ol as the active ingredient in saline was placed in both eyes of all rabbits in the experimental group. Rabbits in the control group received 50 μl of saline drops in both eyes. Thirty minutes later intraocular pressure was again measured and 3.5 mg of caffeine/kg of body weight was injected into the marginal ear vein. One hour after the caffeine injection, the intraocular pressure was read in both eyes using a pneumotonograph.

One hour after caffeine injection, both eyes of rabbits in the control group showed ocular hypertension. Compounds of this invention when applied to the rabbit eye prior to experimental inducement of increased intraocular pressure were able to prevent such hypertension. The difference between the control group and the experimental group was significant. (p<0.01)

What is claimed is:

1. A method for treatment of increased intraocular pressure in a mammal, which method comprises topical applicaiton to the eye of a mammal in need of such treatment of an acceptable pharmaceutical ophthalmic composition containing 0.001–1% wt./vol of a compound chosen from those represented by the formula:

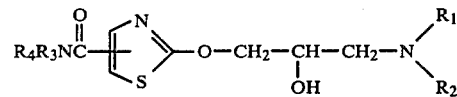

and their pharmaceutically acceptable, non-toxic salts wherein $R_1$ and $R_2$ are each independently selected from the group of hydrogen, lower alkyl, lower cycloalkyl, lower alkenyl, phenyl optionally substituted, and lower phenylalkyl;

$R_3$ and $R_4$ are each independently selected from the group of hydrogen, linear or branched alkyl, cycloalkyl, and phenyl; and wherein $R_4R_3NC(O)$ is a substituent on the thiazole ring at either the 4or - 5- position.

2. The method of claim 1 for treatment of glaucoma.

3. The method of claim 2 wherein one of $R_1$ or $R_2$ is hydorgen and the other is isopropyl, sec-butyl, t-butyl, cyclopropyl, or cyclopentyl; $R_3$ is hydrogen; and $R_4$ is 5-methylhexyl, 4-methylhexyl, n-heptyl or n-hexyl.

4. The method of claim 3 wherein said compound is selected from the group consisting of 1-t-butylamino-3-(5-5-methylhexylaminocarbonylthiazol-2-oxy)-2-proponol and pharmaceutically acceptable salts and esters thereof.

5. A method for treatment of increased intraocular pressure in a mammal which method comprises topical application to the eye of a mammal in need of such treatment of a pharmaceutical ophthalmic composition containing 0.001–1% wt/vol of a compound chosen from those represented by the formula:

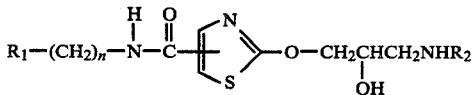

and pharmaceutically acceptable, non-toxic salts thereof wherein
n is the integer 2, 3, or 4;
$R_1$ is a carbocycle selected from the group consisting of bicyclo[3.1.0]hexyl, bicyclo[2.2.1]heptyl, adamantyl, and 4-methylbicyclo-[2.2.2]oct-1-yl; and wherein attachment to the $(CH_2)_n$ linking group can be at any ring atom of bicyclohexyl, bicycloheptyl, or adamantyl groups and is at the 1-position of the bicyclooctytyl group; and
$R_2$ is lower alkyl.

6. The method of claim 5 for treatment of glaucoma.

7. The method of claim 5 wherein n is 2 and $R_2$ is selected from the group of isopropyl and t-butyl.

8. The method of claim 7 wherein $R_2$ is isopropyl.

9. The method of claim 8 where in $R_1$ is bicyclo[3.1.0-]hex-6-yl and said compound is selected from the group consisting of 1-isopropylamino-3-(5-[2-(endobicyclo[3.1.0]hex-6-yl)ethylaminocarbonyl]thiazol-2-yloxy)-propan-2-ol and pharmaceutically acceptable, non-toxic salts thereof.

10. The method of claim 7 wherein $R_2$ is t-butyl.

11. The method of claim 10 wherein $R_1$ is bicyclo[3.1.0]hex-6-yl and said compound is selected from the group consisting of 1-t-butylamino-3-(5-[2-(endobicyclo[3.1.0]hex-6yl)ethylaminocarbonyl]thiazol-2-yloxy)-propan-2-ol and pharamceutically acceptable, non-toxic salts thereof.

* * * * *